United States Patent [19]

Tsuda et al.

[11] Patent Number: 5,202,476
[45] Date of Patent: Apr. 13, 1993

[54] PURIFICATION OF 2-KETO-L-GULONIC ACID

[75] Inventors: Masahiko Tsuda, Kobe; Kimio Iwai, Takatsuki, both of Japan

[73] Assignee: Takeda Chemical Industries, Ltd., Osaka, Japan

[21] Appl. No.: 692,788

[22] Filed: Apr. 29, 1991

Related U.S. Application Data

[63] Continuation of Ser. No. 343,257, Apr. 26, 1989, abandoned.

[30] Foreign Application Priority Data

Apr. 29, 1988 [JP] Japan ................................ 63-106731

[51] Int. Cl.$^5$ ..................... C07C 51/00; C07C 59/147
[52] U.S. Cl. ..................................... 562/513; 562/577
[58] Field of Search ................................ 562/577, 513

[56] References Cited

U.S. PATENT DOCUMENTS 3,381,027  4/1968  Jaffe et al. ............................ 562/577

FOREIGN PATENT DOCUMENTS 38-8714  6/1963  Japan ................................... 562/577

Primary Examiner—José G. Dees
Assistant Examiner—Joseph M. Conrad, III
Attorney, Agent, or Firm—Wenderoth, Lind & Ponack

[57] ABSTRACT

According to the present invention which comprises subjecting an aqueous solution of 2-keto-L-gulonic acid or its water-soluble salt containing an acid impurity, whose acidity is higher than that of 2-keto-L-gulonic acid, to contact with an anion-exchange resin, then allowing the 2-keto-L-gulonic acid or the water-soluble salt thereof to precipitate from the processed solution obtained by allowing the impurity to be adsorbed, 2KGA or its water-soluble salt of a high purity can be separated in a high yield from an aqueous solution of 2KGA or its water-soluble salt containing acid impurities with less number of steps as compared with conventional methods.

9 Claims, No Drawings

PURIFICATION OF 2-KETO-L-GULONIC ACID

This application is a continuation of now abandoned application, Ser. No. 07/343,257 filed on Apr. 26, 1989 now abandoned.

This invention relates to a method of purifying 2-keto-L-gulonic acid which is useful as an intermediate for the synthesis of L-ascorbic acid.

As methods for producing L-ascorbic acid from 2-keto-L-gulonic acid, there have been known, among others, the method which comprises subjecting 2-keto-L-gulonic acid to esterification with methanol by using diazomethane, dimethyl sulfate, etc., then by allowing the ester to react with methylate in methanol to produce the corresponding sodium salt, followed by subjecting the sodium salt to decomposition with hydrochloric acid [Progress of Vitaminology, Second Series, Compiled by Japan Vitamin Academy (1960), p.123 to 124] or the method which comprises allowing a mineral acid to act on 2-keto-L-gulonic acid in the presence of an inert solvent and a surfactant to thereby directly enolize 2-keto-L-gulonic acid to give L-ascorbic acid (Japanese Patent Publication No. 48-15931). These reactions for synthesizing L-ascorbic acid may, anyhow, proceed by employing 2-keto-L-gulonic acid as a free acid or a metal salt such as sodium salt or calcium salt. However, in the case of employing the metal salt, the amount of a mineral acid and the amount of alkali to be used for neutralization become larger, and a complicated process is necessary for separating the by-produced salt, thus inevitably inviting the lowering of L-ascorbic acid. Therefore, for producing L-ascorbic acid with an industrial advantage, it is most preferable to employ the synthetic intermediate, 2-keto-L-gulonic acid as a free acid. Hereinafter, the free acid of 2-keto-L-gulonic acid is sometimes simply called 2KGA.

Generally reviewing the known techniques from such viewpoints as above, there are found, as the methods concerning the separation of 2-keto-L-gulonic acid contained in the fermentation broth, those of separating sodium salt of 2KGA (Japanese Patent Publication Nos. 52-66684, 52-66685, 53-62894) and, as those of separating 2KGA, there are found such methods as follows. (1) A method for separating 2KGA, which comprises subjecting the fermentation broth to filtration and then concentration to precipitate the calcium salt of 2-keto-L-gulonic acid, separating the calcium salt, processing the calcium salt with sulfuric acid to remove the gypsum, concentrating the solution, then separating precipitating 2KGA. (U.S. Pat. Nos. 2,421,611 and 2,421,612).

(2) A method for separating 2KGA, which comprises subjecting the fermentation broth to filtration, processing the filtrate with a cation-exchange resin (H-type), concentrating the processed filtrate to precipitate 2KGA, then separating the precipitated 2KGA (Japanese Patent Publication No. 41-5907).

(3) A method for separating 2KGA, which comprises the following processes: The fermentation broth is subjected to filtration, and the filtrate is allowed to pass through Amberlite 200 (H-type) resin, then the effluent is allowed to pass through Amberlite XE-168 so that 2KGA is allowed to be adsorbed on the resin. Elution of 2KGA is then carried out by using 1N-aqueous ammonia, and the eluate is concentrated under reduced pressure. To the concentrate is added an activated charcoal to decolorize, then the resultant is processed with Amberlite-200 to adjust the pH at about 1.5. To the solution is added calcium hydroxide to adjust the pH at 6.0 to 6.5, which is then subjected to filtration. The filtrate is again processed with Amberlite-200 resin to adjust the pH at about 1.5, and 2KGA is then allowed to be adsorbed on Amberlite XE-168, followed by elution thereof with 0.1N-aqueous ammonia. The eluate is then processed with Amberlite IR-200 (H-type) to remove ammonia, and then concentrated under reduced pressure to separate 2KGA (Japanese Patent Publication No. 51-40154).

The object of this invention is the provision of a method for separating in a high yield 2KGA of a high quality, which is advantageously employed for the synthesis of L-ascorbic acid, from a fermentation broth.

While referring to this object, the afore-mentioned known techniques of separating 2KGA are discussed as follows.

The method (1) comprises complexed processes such as precipitation and separation of calcium salt, precipitation and separation of gypsum, and further precipitation and separation of 2KGA, besides the filtration of fermentation broth, and the yield is thus inevitably low. And, as the solubility of the calcium salt is high, when it is intended to allow the calcium salt to precipitate by concentration to a great extent, the viscosity of the solution increases to result in the poor growth of crystals to give only fine ones, which makes it remarkably difficult to separate the crystals. Further, as gypsum still remains in the state of solution in the filtrate precipitates by concentration, separation of crystals of 2KGA is hampered to cause inevitably lowering of the product quality. As described thus above, the method (1) can be hardly considered as being industrially advantageous.

In the method (2), as the fermentation broth contains various impurities including insoluble impurities such as cell bodies, metallic ion, etc., the filtration of the fermentation broth and processing with a cation-exchange resin (H-type) are not enough to remove these impurities, and the viscosity of the solution increases so that the growth of crystals is inhibited resulting in the production of only fine crystals, thus the separation of the crystals is remarkably difficult, which lowers the quality and the yield of crystals. As described above, the method (2) can be hardly considered as being industrially advantageous.

The method (3) requires, besides the filtration of the fermentation broth and the process with Amberlite-200 (H-type), too complicated processes, thus it is not practicable and industrially disadvantageous.

In view of such circumstances as mentioned above, the present inventors made diligent studies with an object of separating 2KGA of a high quality in a high yield from a fermentation broth containing 2KGA or its water-soluble salt, and, as the result, they found that it was remarkably important and essential, in the precipitation of 2KGA, to maintain the content of anionic so as not to exceed a certain given amount, resulting in the accomplishment of the present invention.

The present invention relates to a method for purifying 2-keto-L-gulonic acid or a water-soluble salt thereof, which is characterized by subjecting an aqueous solution of 2-keto-L-gulonic acid or its water-soluble salt containing an acid impurity whose acidity is higher than that of 2-keto-L-gulonic acid to contact with an anion-exchange resin, then allowing the 2-keto-L-gulonic acid or the water-soluble salt thereof to precipitate from the processed solution obtained by allowing the impurity to be adsorbed.

As the water-soluble salt of 2-keto-L-gulonic acid, a sodium salt, potassium salt or calcium salt is mentioned.

In the method of this invention, as the aqueous solution of 2KGA or its water-soluble salt to be contacted with an anion-exchange resin (hereinafter sometimes simply referred to as "starting solution"), for example, a fermentation broth containing 2KGA or its water-soluble salt can be used. Such fermentation broth can be, obtained by the method disclosed in Japanese Unexamined Patent Laid-open No. 62-228288 (European Patent Publication 0221707), which is the microbial fermentation, or an aqueous solution containing 2KGA or its water-soluble salt, obtained by the method described in [Progress of Vitaminology, Second Series, Compiled by Japan Vitamin Academy (1960), p.121], which is a synthetic process. The purification method of the present invention is applied especially to the fermentation broth advantageously.

The fermentation broth contains various impurities including insoluble impurities such as cell bodies, organic salts such as organic acids, amino acids, etc., a variety of inorganic salts, pigments, etc. Among these impurities, insoluble ones such as cell bodies or hardly soluble salts such as calcium oxalate, calcium phosphate, are preferably eliminated previously by per se known means e.g. centrifugation, filtration, etc. And, metallic ions or other cationic impurities are preferably decationized by contacting them with a cation-exchange resin (H-type).

Especially, it is preferable that the fermentation broth is subjected to filtration or centrifugation to remove insoluble impurities and hardly soluble salts, then the starting solution obtained by contacting the filtrate with a cation-exchange resin is contacted with an anion-exchange resin.

As the above-mentioned method comprising the contact with an anion-exchange resin and with a cation-exchange resin, mention is made of either the column method or the batch method, and the former is more preferable for carrying out the present invention on an industrial scale.

The following is the description of the ion-exchange resin employed in the present invention.

As the anion-exchange resin, use is made of any of strongly, moderately or weakly basic ones, and use of weakly basic ones is preferable in general, which are exemplified by Diaion WA-30 (OH-type), WA-21 (OH-type), PA-318 (OH-type) PA-412 (OH-type) [manufactured by Mitsubishi Chemical Industries, Ltd.], Amberlite IRA-35 (OH-type), Amberlite IRA-94 (OH-type) [manufactured by Rohm & Haas Co., USA], Dowex 66 (OH-type), Dowex MWA-1 (OH-type) [manufactured by Dow Chemical Co., USA], etc.

As the cation-exchange resin, either strongly acid ones or weakly acid ones may be employed, and use of the former ones is preferable in general, which are exemplified by Amberlite 200C (H-type) [manufactured by Rohm & Haas Co., USA], Diaion SK1B (H-type), PK216 (H-type) [manufactured by Mitsubishi Chemical Industries, Ltd.], Dowex 50W (H-type), Dowex 88 (H-type) and MSC-1 (H-type) [manufactured by Dow Chemical Co., USA], etc.

Hereinafter, the solution contacted with an anion-exchange resin (OH-type) and the anionic impurities are abbreviated as "processed solution" and "AI", respectively. And, AI and, the ratio thereof in 2KGA ,"R" are defined as follows.

A fermentation broth containing 2-keto-L-gulonic acid is subjected to filtration or centrifuge. The resulting aqueous solution of 2KGA or its water-soluble salt is decationized with a cation-exchange resin (H-type) to obtain the starting solution. The starting solution is subjected to neutralization titration to determine the equivalence of acid, which is defined as the total acid equivalent concentration [TA](g-eq/l). The same solution is subjected to HPLC to determine the amount of 2KGA, on the basis of which the acid equivalent concentration of 2KGA was calculated [2KGA](g-eq/l). The equivalent concentration of AI [AI](g-eq/l) and the ratio of AI in 2KGA are respectively expressed as follows.

$$[AI] = [TA] - [2KGA] \; (g-eq/l)$$

$$R = \{[AI]/[2KGA]\} \times 100 \; (\%)$$

R represents an equivalent ratio of an acid impurity relative to 2KGA.

In general, R of the aqueous solution obtained by subjecting a fermentation broth containing 2KGA or its water-soluble salt to filtration or centrifuge to remove insoluble impurities such as cell bodies and hardly soluble salts is 30% or more. In the present invention, said fermentation broth itself can be used as the starting solution. And, R of the processed solution is made, in general, to be about 30% or less by contacting the starting solution with an anion-exchange resin.

The R of the fermentation broth is generally about 40 to 70%. The acid impurity contains one whose acidity is higher than that of 2KGA in an amount of about 50 to 90% relative to the R. In the present invention, the acid impurity whose acidity is higher than that of 2KGA, should be absorbed by contacting the anion-exchange resin.

The following is the explanation of the amount of the anion-exchange resin employed in the present invention. While the resin amount varies with conditions such as the value of R in the starting solution, the volume of the starting solution, the anion-exchange capacity of the resin employed, it is generally desirable that, for example, the starting solution whose R is about 30 to 200(%) is contacted with a weakly basic anion-exchange resin [Diaion WA-30 (OH-type), exchange capacity: 1.5(meq/ml) or higher] so that the AI equivalent may be about 2 to 5 (g−eq/l-resin) relative to 1 l of resin. Incidentally, the less the value of R of the processed solution, the higher becomes the yield of 2KGA in the precipitation process. When, however, R becomes about 10% or lower, 2KGA is adsorbed on an anion-exchange resin to lower the yield of 2KGA when contacting with the resin, and therefore, it is generally preferable to have R ranged within 10% to 25%.

And, in the case of employing the starting solution whose R is less than about 30%, R can be lowered by contacting the starting solution with an anion-exchange resin so that the 2KGA crystals of higher crystal purity can be obtained.

The thus-obtained processed solution may be subjected to decolorization treatment by using an activated charcoal or a decolorizing resin, upon necessity.

According to the purification method of the present invention, 2KGA or its water-soluble salt of a high purity, can be separated in a high yield from an aqueous solution of 2KGA or its water-soluble salt containing acid impurities with less number of steps as compared with conventional methods.

By the following reference examples, experimental examples and working examples, the present invention is described in further detail. The fermentation broth employed herein is that prepared by the method disclosed in the reference examples given below.

REFERENCE EXAMPLE 1

In a 2 l-capacity Sakaguchi flask was put 500 ml of a pre-culture medium composed of 2.0% of glucose, 1.0% of peptone, 1.0% of dry yeast, 2.0% of calcium carbonate and 0.01% of Actocol (antifoaming agent, manufactured by Takeda Chemical Industries, Ltd.), and the medium was steam-sterilized at 120° C. for 20 minutes. This Sakaguchi flask was inoculated with 2-keto-L-gulonic acid-producing microorganisms, *Pseudogluconobacter saccharoketogenes* TH 14-86 strain (IFO 14466, FERM BP-1128), and cultivation was carried out at 28° C. for 3 days by reciprocal-shaking (85 spm) to obtain a pre-culture broth.

In a 50 l-capacity fermenter was put 30 l of a seed culture medium (pH 6.5) composed of 3.0% of glucose, 1.0% of CSL, 0.5% of dry yeast, 0.05% of sodium thiosulfate, 0.1% of ferrous sulfate, 2.0% of calcium carbonate and 0.03% of Actocol, and the medium was steam-sterilized at 125° C. for 30 minutes. The pre-culture broth (500 ml) obtained as above was transplanted into this fermenter, and it was incubated for three days at 30° C. under the inner pressure of 1.0 $kg/cm^2G$ with aeration of 30 l/min. while stirring at 200 rpm to obtain a seed-culture broth. On the other hand, *Bacillus megaterium* IFO 12108, which was a concomitantly-mixed bacterium, was inoculated into 500 ml of the above-mentioned pre-culture medium contained a 2 l-capacity Sakaguchi flask, which was incubated at 28° C. for two days under reciprocal shaking (85 spm) to obtain a seed culture broth of *Bacillus megaterium*.

In a 200 l-capacity fermenter was put 65 l of a culture medium composed of 3 kg of L-sorbose (sterilized in advance), 7 kg of calcium carbonate, 2 kg of CSL, 300 g of dry yeast, 300 g of ammonium sulfate, 500 g of sodium thiosulfate, 100 g of ferrous sulfate, 30 g of Actocol and water. The medium was steam-sterilized at 125° C. for 30 minutes. To this fermenter were transplanted 10 l of the above-mentioned seed culture broth of *Pseudogluconobacter saccharoketogenes* TH 14-86 strain and 500 ml of the seed culture solution of the concomitantly-mixed bacterium, *Bacillus megaterium* IFO 12108 strain, and incubation was initiated at 30° C. under an inner-pressure of 1.0 $kg/cm^2G$ with aeration of 80 l/min. while stirring (200 rpm). On the other hand, 15 kg of L-sorbose was dissolved in water to make 30 l of the solution. The solution was steam-sterilized at 120° C. for 20 minutes. To this was added an aqueous solution of sorbose continuously, starting at the 6th hour after initiating the incubation, finishing to add the whole volume in 36 hours. After completing the addition of sorbose, the incubation was conducted for further 28 hours under the above-mentioned conditions. By the incubation for 70 hours in total was obtained fermentation broth containing 2-keto-L-gulonic acid.

REFERENCE EXAMPLE 2

In a 200 l-capacity fermenter was put 100 l of a fermentation medium composed of 11.5% of L-sorbose (sterilized in advance), 0.3% of dry yeast, 3.0% of CSL, 0.1% of sodium thiosulfate, 0.2% of ferrous sulfate and 1.0% of calcium carbonate, which was steam-sterilized at 125° C. for 30 minutes. To this fermenter was transplanted 10 l of a seed-culture broth of *Pseudogluconobacter saccharoketogenes* TH 14-86 strain. While controlling the pH of the fermentation broth with 20% caustic soda, incubation was carried out for 4 days at 30° C. with aeration of 80 l/min. under an inner-pressure of 1.0 $kg/cm^2G$ while stirring (200 rpm) to obtain a fermentation broth containing 2-keto-L-gulonic acid.

REFERENCE EXAMPLE 3

In a 2 l-capacity Sakaguchi flask was put 500 ml of a pre-culture medium composed of 2.0% of glucose, 1.0% of peptone, 1.0% of dry yeast, 2.0% of calcium carbonate and 0.01% of Actocol (antifoaming agent, manufactured by Takeda Chemical Industries, Ltd.), and the medium was steam-sterilized at 120° C. for 20 minutes. This Sakaguchi flask was inoculated with 2-keto-L-gulonic acid-producing microorganisms, *Pseudogluconobacter saccharoketogenes* TH 14-86 strain (IFO 14466, FERM BP-1128), and cultivation was carried out at 28° C. for 3 days by reciprocal-shaking (85 spm) to obtain a pre-culture broth.

In a 500 l-capacity fermenter was put 360 l of a seed culture medium (pH 6.5) composed of 3.0% of glucose, 1.0% of CSL, 0.5% of dry yeast, 0.05% of sodium thiosulfate, 0.1% of ferrous sulfate, 2.0% of calcium carbonate and 0.03% of Actocol, and the medium was steam-sterilized at 125° C. for 30 minutes. The pre-culture broth (1 l) obtained as above was transplanted into this fermenter, and it was incubated for three days at 30° C. under the inner pressure of 1.0 $kg/cm^2G$ with aeration of 180 l/min. while stirring at 200 rpm to obtain a seed-culture broth. On the other hand, *Bacillus megaterium* IFO 12108, which was a concomitantly-mixed bacterium, was inoculated into a 2 l-capacity Sakaguchi flask contained 500 ml of the above-mentioned pre-culture medium, and it was incubated at 28° C. for two days under reciprocal shaking (85 spm) to obtain a seed culture broth of *Bacillus megaterium*.

In a 50 l-capacity fermenter was put 30 l of the above-mentioned pre-culture medium, and it was steam-sterilized at 125° C. for 30 minutes. To this fermenter were transplanted 500 ml of the above-mentioned pre-culture broth of *Bacillus megaterium* IFO 12108 strain, and it was incubated at 28° C. under an inner-pressure of 1.0 $kg/cm^2G$ with aeration of 15 l/min. while stirring (250 rpm) to obtain a seed culture broth of *Bacillus magaterium*.

In a 6 $m^3$-capacity fermenter was put 2200 l of a medium composed of 108 kg of L-sorbose (sterilized in advance), 252 kg of calcium carbonate, 72 kg of CSL, 10.8 kg of dry yeast, 10.8 kg of ammonium sulfate, 1.8 kg of sodium thiosulfate, 3.6 kg of ferrous sulfate, 1.0 kg of Actocol and water. The medium was steam-sterilized at 125° C. for 30 minutes. To this fermenter were transplanted 360 l of the above-mentioned seed culture broth of *Pseudogluconobacter saccharoketogenes* TH14-86 strain and 20 l of the seed culture broth of the concomitantly-mixed bacterium, *Bacillus megaterium* IFO12108 strain, and incubation was initiated at 30° C. under an inner-pressure of 1.0 $kg/cm^2G$ with aeration of 1800 l/min. while stirring (90 rpm).

On the other hand, 540 kg of L-sorbose was dissolved in water to make 1100 l of the solution. The solution was steam-sterilized at 120° C. for 20 minutes and then added to the fermenter, starting at the 6th hour after initiating the incubation, finishing to add the whole volume in 36 hours.

After completing the addition of sorbose, the incubation was conducted for further 30 hours under the above-mentioned conditions. By the incubation for 72 hours in total was obtained fermentation broth containing 2-keto-L-gulonic acid (142 g/l).

REFERENCE EXAMPLE 4

Under an inner pressure of about 0 kg/cm$^2$G in the fermenter, incubation was initiated in the same manner as that of the Reference Example 3. The inner pressure was raised with the progress of the fermentation, to be 1.0 kg/cm$^2$G finally and the incubation was carried out for 66 hours, to obtain a fermentation broth containing the same amount of 2-keto-L-gulonic acid as that in the Reference Example 3.

EXPERIMENTAL EXAMPLE

To 60 l of the fermentation broth obtained by the method described in the Reference Example 1 was added sulfuric acid to adjust the pH to 1.5, then insolubles were filtered off, and the filtrate was passed through a column packed with 5 l of Amberlite 200C (H-type). The starting solution of a volume of 77.5 l combined with a solution extruded with water was obtained, which contained 8,156 g (42.0 g-eq) of 2KGA, 23.5 g-eq of AI, respectively, and the R was 56.0%. This starting solution was divided into 5 fractions, and they were processed respectively as in the following manner to separate 2KGA. (1) First fraction: 4.0 l of the starting solution (containing 421.0 g of 2KGA) was, while stirring, concentrated under reduced pressure at 39° to 41° C. until it became 75% (w/v %) in terms of 2KGA, followed by cooling to 5° C. taking 12 hours. The crystals were separated from the mother liquor by means of a centrifugal machine [Kokusan Enshinki Corp., Type H-110A, 3,000 rpm], which were washed by spraying 80 ml of water of 5° C. The viscosity of the mother liquor was 65 centipoise (20° C.), and the pH thereof was 0.4. The wet crystals were dried at 30° C. under reduced pressure to obtain 388.2 g of the first crop of crystals. The amount of 2KGA contained in the first crop of crystals was 332.6 g, and the purity thereof based on the anhydride (hereinafter simply referred to as purity) was 93.3%. The mother liquor and the washing were combined, and the mixture was concentrated under reduced pressure at 39° to 41° C. while stirring until it became 55% (w/v %) in terms of 2KGA, followed by cooling to 5° C. in the course of 12 hours. Then, the crystals were separated from the mother liquor by means of the above-mentioned centrifugal machine, and the crystals were washed by spraying 20 ml of water of 5° C. The viscosity of the mother liquor was 320 centipoise (20° C.), and the pH thereof was 0.1. The wet crystals were dried at 30° C. under reduced pressure to obtain 37.8 g of the second crop of crystals. The amount of 2KGA contained in the second crop of crystals was 29.9 g, and the purity thereof was 85.9%. The first and second crops of crystals were combined. The precipitation yield and the crystal purity were 86.1% and 92.6%, respectively.

(2) Second fraction: 27.2 l of the starting solution (containing 2,862 g of 2KGA) was passed through a column packed with 1.7 l of Diaion WA-30 (OH-type). The processed solution of a volume of 30.6 l combined with the solution extruded with water was obtained, and it contained 2,860 g (14.7 g-eq) of 2KGA and 4.30 g-eq of AI, respectively, and The R was 29.3%. Then, 4.50 l of the processed solution (containing 421.0 g of 2KGA) was taken, and it was treated in a manner similar to that of (1) to obtain 373.8 g of the first crop of crystals (containing 331.7 g of 2KGA, purity: 96.8%). The viscosity of the mother liquor was 30 centipoise (20° C.), and the pH thereof was 0.9. And, 52.1 g of the second crop of crystals (containing 43.8 g of 2KGA, purity: 91.7%) was obtained. The viscosity of the mother liquor was 60 centipoise (20° C.), and the pH thereof was 0.7. The first and second crops of crystals were combined. The precipitation yield and the crystal priority were 89.2% and 96.2%, respectively.

(3) Third fraction: 22.1 l of the starting solution (containing 2,326 g of 2KGA) was processed with Diaion WA-30 (OH-type) in a manner similar to that of (2) to obtain 25.5 l of the processed solution, and it contained 2,303 g (11.9 g-eq) of 2KGA and 2.86 g-eq of AI, respectively, and the R was 24.0%. Then, 4.66 l of the processed solution (containing 421.0 g of 2KGA) was taken, and it was treated in a manner similar to that of (1) to obtain 365.0 g of the first crop of crystals (containing 328.8 g of 2KGA, purity: 98.3%). The viscosity of the mother liquor was 15 centipoise (20° C.), and the pH thereof was 1.1. And, 63.5 g of the second crop of crystals (containing 54.7 g of 2KGA, purity: 94.2%) was obtained. The viscosity of the mother liquor was 32 centipoise (20° C.), and the pH thereof was 1.0. The first and the second crops of crystals were combined. The precipitation yield and the crystal purity were 91.1% and 97.7%, respectively.

(4) Fourth fraction: 13.6 l of the starting solution (containing 1,431 g of 2KGA) was processed with Diaion WA-30 (OH-type) in a manner similar to that of (2) to obtain 17.0 l of the processed solution, and it contained 1,374 g (7.08 g-eq) of 2KGA and 0.885 g-eq of AI, respectively, and the R was 12.5%. Then, 5.21 l of the processed solution of the processed solution (containing 421.0 g of 2KGA) was taken, and it was treated in a manner similar to that of (1) to obtain 357.4 g of the first crop of crystals (containing 327.1 g of 2KGA, purity: 100%). The viscosity of the mother liquor was 10 centipoise (20° C.), and the pH thereof was found to be 1.4. And, 74.6 g of the second crop of crystals (containing 66.5 g of 2KGA, purity: 97.2%) was obtained. The viscosity of the mother liquor was 19 centipoise (20° C.), and the pH thereof was 1.3. The first and second crops of crystals were combined. The precipitation yield and the crystal purity were 93.5% and 99.7%, respectively.

(5) Fifth fraction: 6.80 l of the starting solution (containing 715.6 g of 2KGA) was processed with Diaion WA-30 (OH-type) in a manner similar to that of (2) to obtain 10.2 l of the processed solution, and it contained 566.8 g (2.92 g-eq) of 2KGA and 0.162 g-eq of AI, respectively, and the R was 5.55%. Then, 7.58 l of the processed solution (containing 421.2 g of 2KGA) was taken, and it was treated in a manner similar to that of (1) to obtain 355.0 g of the first crop of crystals (containing 324.3 g of 2KGA, purity: 100%). The viscosity of the mother liquor was 7 centipoise (20° C.), and the pH thereof was found to be 1.4. Further, 87.9 g of the second crop of crystals (containing 78.4 g of 2KGA, purity: 97.5%) was obtained. The viscosity of the mother liquor was 11 centipoise (20° C.), and the pH thereof was 1.3. The first and the second crops of crystals were combined. The precipitation yield was 95.6% and the crystal purity was 99.5%.

These results were shown in Table 1.

TABLE 1

| fraction | starting solution R (%) | treatment with anion-exchange resin | | processed solution R (%) | precipitation[2] | |
|---|---|---|---|---|---|---|
| | | amount treated[1] | yield (%) | | yield (%) | crystal purity (%) |
| first | 56.0 | — | — | — | 86.1 | 92.6 |
| second | 56.0 | 4.85 | 99.9 | 29.3 | 89.2 | 96.2 |
| third | 56.0 | 3.94 | 99.0 | 24.0 | 91.1 | 97.7 |
| fourth | 56.0 | 2.42 | 96.0 | 12.5 | 93.5 | 99.7 |
| fifth | 56.0 | 1.21 | 79.2 | 5.6 | 95.6 | 99.5 |

Note
[1] The amount of AI in the starting solution fed relative to 1 l of anion-exchange resin (OH-Type) (unit: AI g-eq/1 l of Resin)
[2] The precipitation yield of the first crop of crystals combined with the second crop of crystals, and the crystal purity of the anhydride.

As is apparent from Table 1, in the first fraction, while crystals of 2KGA were obtained by concentrating the starting solution prepared by subjecting the fermentation broth to filtration and then processing the filtrate with cation-exchange resin (H-type), the separation of crystals from the mother liquor was remarkably difficult, and the precipitation yield and the crystal purity were remarkably low. In the second to the fifth fractions, the starting solution was processed with an anion-exchange resin (OH-type) to remove AI partially, followed by concentration to allow 2KGA to crystallize. In the second, third and fourth fractions, the less the amount of the starting solution to be processed with an anion-exchange resin was, the less the ratio of AI to 2KGA was, thus the separability of crystals from AI was improved, resulting in raising the precipitation yield and the crystal purity. However, as seen in the case of the fifth fraction, when a lesser amount of the starting solution was used, the ratio of AI in the processed solution relative to 2KGA further decreased, but when it was processed with an anion-exchange resin, a part of 2KGA was adsorbed in the resin, thus the total yield obtained from the processing with an anion-exchange resin and from precipitation was lowered.

From the foregoing, when the starting solution having a high ratio of AI relative to 2KGA is concentrated as it is to thereby allow 2KGA to crystallize therefrom, the separation of the crystals from the mother liquor is remarkably difficult and, besides, the precipitation yield and the crystal purity becomes lower, thus being undesirable as a method to be conducted on an industrial scale. It is apparent, however, that when the starting solution is processed with an anion-exchange resin (OH)-type to such an extent as to cause no substantial adsorption loss of 2KGA and also when the ratio of AI relative to 2KGA is controlled to be, in general, not exceeding about 30%, preferably 20% or lower, 2KGA of a high quality can be separated in a high yield.

WORKING EXAMPLE 1

7.0 l of fermentation broth (containing 1,006 g of 2KGA) obtained by the method shown in the Reference Example 1 was subjected to filtration to remove insolubles, 8.45 l of the filtrate combined with the washing was passed through a column packed with 6.0 l of Amberlite 200C (H-type) to obtain 16.0 l of the starting solution combined with the solution extruded with water. In the starting solution were contained 922.8 g (4.75 g-eq) of 2KGA and 2.54 g-eq of AI, respectively, and the R was 53.5%. 12.84 l of the said starting solution was divided into two portions, and each portion was treated as follows.

(1) 6.42 l of the starting solution (containing 370.0 g of 2KGA) was passed through a column packed with 0.35 l of Diaion WA-30 (OH-type) (2.91 g-eq/l-resin as AI) to obtain 7.12 l of the processed solution combined with the solution extruded with water. In the processed solution were contained 368.0 g (1.90 g-eq) of 2KGA and 0.370 g-eq of AI, respectively, and the R value was 19.5%. This processed solution was, while stirring, concentrated under reduced pressure at 39° to 41° C. to make it to be about 70% w/v in terms of 2KGA to thereby allow 2KGA to precipitate, followed by cooling to 5° C. for 12 hours while stirring. By means of the same centrifugal machine as employed in the Experimental Example, the crystals were separated from the mother liquor and washed by spraying 70 ml of water of 5° C. The wet crystals were dried at 30° C. under reduced pressure to obtain 304.3 g of the first crop of crystals. The content of 2KGA in the first crop of crystals was 277.8 g and the purity thereof was 99.9%. The mother liquor combined with the washing was concentrated under reduced pressure at 39° to 41° C. until it became about 50% w/v in terms of 2KGA to thereby allow 2KGA to precipitate, followed by cooling to 5° C., while stirring for 12 hours. By means of the same centrifugal machine as employed in the Experimental Example, the crystals were separated from the mother liquor and washed by spraying thereon 20 ml of water of 5° C. The wet crystals were dried under reduced pressure at 30° C. to obtain 68.1 g of the second crop of crystals containing 61.1 g of 2KGA, whose purity was 98.1%.

(2) 6.42 l of the starting solution (containing 370.0 g of 2KGA) was, in a manner similar to that of (1), concentrated to cause precipitation and the the crystals were separated to recover 2KGA. The first crop of the crystals was in an amount of 329.4 g (containing 284.2 g of 2KGA, purity: 94.1%) and the second crop of crystals was in an amount of 33.8 g (containing 27.0 g of 2KGA, purity: 86.2%).

WORKING EXAMPLE 2

40 l of the fermentation broth obtained by the method shown in Reference Example 2 was subjected to filtration with the ceramics filter [Toshiba Ceramics Ltd., MEMBRALOX multi-type media P19 X L750 mm, µ] to remove insolubles to leave 56 l of a clear filtrate. 8.35 l of the filtrate was taken, which was allowed to pass through a column packed with 5.5 l of Diaion SK1B (H-type) to obtain 19.4 l of the starting solution combined with the solution extruded with water. The starting solution contained 848.0 g (4.37 g-eq) of 2KGA and 2.54-eq of AI, respectively, and R was found to be 58.1%. 18.3 l of the starting solution was divided into two portions, and each portion was treated as follows.

(1) 9.15 l of the starting solution (containing 400.0 g of 2KGA) was allowed to pass through a column packed with 0.30 l of Diaion PA318 (OH-type) [3.99 g-eq/l-Resin as AI] to obtain 9.75 l of the processed solution, in which were contained 399.0 g (2.06 g-eq) of 2KGA and 0.493 g-eq of AI, respectively, and the R value was 24.0%. This processed solution was, in a manner similar to that in the Working Example 1(1), subjected to concentration to cause precipitation and separation of crystals to recover 2KGA. The amount of the first crop of crystals was 325.2 g (containing 296.5 g of 2KGA, purity: 99.6%) and that of the second crop of crystals was 83.4 g (containing 75.0 g of 2KGA, purity: 98.3%).

(2) 9.15 l of the starting solution (containing 400.0 g of 2KGA) was, in a manner similar to that in the Working Example 1(1), subjected to concentration to cause precipitation and separation of crystals to recover 2KGA. The amount of the first crop of crystals was 352.0 g (containing 304.0 g of 2 KGA, purity: 93.9%) and that of the second crop of crystals was 44.6 g (containing 35.2 g of 2KGA, purity: 85.2%).

WORKING EXAMPLE 3

To 1820 l of the fermentation broth obtained by the method described in the Reference Example 3 was added sulfuric acid to adjust the pH to 1.5, then insolubles were removed by filtration using an Oliver-type drum filter (Daiki Gum Industries Co. Ltd., filter area: 4.5 m$^2$) which was pre-coated by 40 kg of the Hyflo Super Cell ® and 20 kg of the Standard Super Cell ®, to obtain 2160 l of the filtrate combined with a solution extruded with water.

The filtrate (1400 l) was passed through a column (35×220 cm) packed with Diaion PK216 (H type, Mitubishi Chemical Industries, Ltd.) to obtain 1710 l of the starting solution combined with a solution extruded with water. In the starting solution were contained 136.8 kg (705 g-eq) of 2KGA and 419 g-eq of AI, respectively, and the R was 59.5%. This starting solution was treated to obtain 2KGA as follows.

(1) 800 l of the starting solution (containing 64.0 kg of 2KGA) was, while stirring, concentrated under reduced pressure at 38°–41° C. until it became 75% (w/v %) in terms of 2KGA, followed by cooling to 5° C. taking 12 hours. The crystals were separated from the mother liquor by means of a centrifugal machine [Matsumoto Kikai Works, Type KM-30] with a nylon screen cloth filter medium, which were washed by spraying 7.0 l of water of 5° C. The wet crystals were dried at 30° C. under reduced pressure to obtain 59.5 kg of the first crop of crystals. The amount of 2KGA contained in the first crop of crystals was 51.3 kg, and the purity was 93.8%. The mother liquor and the washing were combined, and the mixture was concentrated under reduced pressure at 38° to 41° C. while stirring until the volume became 55% (w/v %) in terms of 2KGA, followed by cooling to 5° C. in the course of 12 hours. Then, the crystals were separated from the mother liquor by means of the centrifugal machine with a nylon screen cloth filter medium, and the crystals were washed by spraying 0.5 l of water of 5° C. The wet crystals were dried at 30° C. under reduced pressure to obtain 4.50 kg of the second crop of crystals. The amount of 2KGA contained in the second crop of crystals was 3.50 kg, and the purity thereof was 82.4%. (2) 800 l of the starting solution (containing 64.0 kg of 2KGA) was passed through a column (3.02 g-eq as AI per one liter of resin) packed with 65 L of Diaion PA-412 (OH-type). The starting solution of a volume of 910 l combined with the solution extruded with water was obtained, and it contained 63.4 kg (327 g-eq) of 2KGA and 70.2 g-eq of AI, respectively, and the R was 21.3%. Then, the starting solution was treated in a manner similar to that of (1) to obtain 53.8 kg of the first crop of crystals (containing 48.8 kg of 2KGA, purity: 99.1%) and 10.4 kg of the second crop of crystals (containing 9.30 kg of 2KGA, purity: 98.0%).

What is claimed is:

1. A method for purifying 2-keto-L-gulonic acid or its water-soluble salt, which consists essentially of the steps of contacting an aqueous solution containing 2-keto-L-gulonic acid or its water-soluble salt and an acid impurity whose acidity is higher than that of 2-keto-L-gulonic acid with an anion-exchange resin to obtain a processed solution, wherein at least a portion of the acid impurity in the aqueous solution is adsorbed by the anion-exchange resin, and precipitating the 2-keto-L-gulonic acid or the water-soluble salt thereof from the processed solution, wherein the acid impurity in the processed solution is in an amount of 30% or less in terms of equivalent ratio relative to 2-keto-L-gulonic acid.

2. The method according to claim 1, wherein the aqueous solution of 2-keto-L-gulonic acid or its water-soluble salt is previously allowed to be contacted with a cation-exchange resin to decationize.

3. The method according to claim 2, wherein the cation-exchange resin is a strongly acid one.

4. The method according to claim 3, wherein the cation-exchange resin is Amberlite 200C ® (H-type), Diaion SK1B ® (H-type), Diaion PK216 (H-type) Dowex 50W ® (H-type), Dowex 88 ® (H-type) or Dowex MSC-1 ® (H-type).

5. The method according to claim 1, wherein the amount of acid impurity in the aqueous solution is about 30 to 200% in terms of equivalent ratio relative to 2-keto-L-gulonic acid.

6. The method according to claim 1, wherein the amount of acid impurity in the processed solution is about 10 to 25% in terms of equivalent ratio relative to 2-keto-L-gulonic acid.

7. The method according to claim 1, wherein the anion-exchange resin is Diaion WA-30 ® (OH-type), Diaion WA-21 ® (OH-type), Diaion PA-412 (OH-type) ® Diaion PA-318 (OH-type), Amberlite IRA-35 ® (OH-type), Amberlite IRA-94 ® (OH-type), Dowex 66 ® (OH-type) or Dowex MWA-1 ® (OH-type).

8. The method according to claim 1, wherein the aqueous solution of 2-keto-L-gulonic acid or its water-soluble salt containing an acid impurity is about 30 to 200% in terms of equivalent ratio relative to 2-keto-L-gulonic acid, is contacted with a weakly basic anion-exchange resin whose exchange capacity is 1.5 meq/ml or higher so that the acid impurity equivalent is about 2 to 5 (g-eq/l-resin) relative to 1 l of resin.

9. The method according to claim 1, wherein the water-soluble salt of 2-keto-L-gulonic acid is a sodium salt, potassium salt or calcium salt.

* * * * *